United States Patent [19]

Chen

[11] Patent Number: 4,982,031

[45] Date of Patent: Jan. 1, 1991

[54] ALPHA OLEFINS FROM LOWER ALKENE OLIGOMERS

[75] Inventor: Catherine S. H. Chen, Berkley Heights, N.J.

[73] Assignee: Mobil Oil Corporation, New York, N.Y.

[21] Appl. No.: 467,437

[22] Filed: Jan. 19, 1990

[51] Int. Cl.$^5$ .............................................. C07C 1/20
[52] U.S. Cl. .................................... 208/324; 585/624
[58] Field of Search ................................ 585/324, 640

[56] References Cited

U.S. PATENT DOCUMENTS

| | | |
|---|---|---|
| 3,246,045 | 4/1966 | Hoffman . |
| 3,409,698 | 11/1968 | Illingworth . |
| 3,984,486 | 10/1976 | Macaluso et al. . |
| 4,390,729 | 6/1983 | Oswald . |
| 4,443,638 | 11/1984 | Yates . |
| 4,469,895 | 9/1984 | Knifton . |
| 4,681,979 | 7/1987 | Araki et al. . |
| 4,855,527 | 8/1989 | Page et al. ........................... 585/527 |
| 4,914,254 | 4/1990 | Pelrine ................................ 585/530 |

*Primary Examiner*—Curtis R. Davis
*Attorney, Agent, or Firm*—Alexander J. McKillop; Charles J. Speciale; L. G. Wise

[57] ABSTRACT

Internally unsaturated near linear oligomers of lower olefins are converted into alpha olefins, or 1-alkenes, of essentially the same degree of linearity. The internally unsaturated olefins are the product of lower alkene oligomerization using a surface deactivated zeloite, such as ZSM-5 or ZSM-23, and contain about 1 to 2 methyl branches per twelve (12) carbon atoms. The feedstock is converted to alpha olefin oligomers which also contain approximately 1 to 2 methyl branches per thirteen (13) carbon atoms. The conversion is achieved by hydroformylation of the near linear internal olefins to provide a novel 1-alkanol oligomer structure without further branching of the carbon oligomeric chain. Acetylation of the 1-alkanol followed by deesterification by pyrolysis provides the sought for near linear 1-alkene. The near-linear oligomers of lower olefins so produced comprise vinyl hydrocarbon monomers that can be further oligomerized by cationic and coordination catalysts.

29 Claims, No Drawings

ALPHA OLEFINS FROM LOWER ALKENE OLIGOMERS

This invention relates to a process for the production of near linear higher alpha olefins from olefinic oligomers prepared from lower alkenes More particularly, the invention relates to a process for the conversion of near linear lower alkene oligomers containing internal olefinic unsaturation to alpha olefins by hydroformylation to 1-alkanols of equivalent linearity, followed by esterification and pyrolysis to 1-alkenes. The near linear alpha olefins so produced are useful, inter alia, for the production of high quality synthetic lubricants.

BACKGROUND OF THE INVENTION

Recent work in the field of olefin upgrading has resulted in a catalytic process for converting lower olefins to heavier hydrocarbons. Heavy distillate and lubricant range hydrocarbons can be synthesized over ZSM-5 type catalysts at elevated temperature and pressure to provide a product having substantially linear molecular conformations due to the ellipsoidal shape selectivity of certain medium pore catalysts.

Conversion of olefins to gasoline and/or distillate products is disclosed in U.S. Pat. Nos. 3,960,978 and 4,021,502 (Givens, Plank and Rosinski) wherein gaseous olefins in the range of ethylene to pentene, either alone or in admixture with paraffins are converted into an olefinic gasoline blending stock by contacting the olefins with a catalyst bed made up of a ZSM-5 type zeolite. Particular interest is shown in a technique developed by Garwood, et al., as disclosed in European patent application No. 83301391.5, published Sept. 29, 1983. In U.S. Pat. Nos. 4,150,062; 4,211,640 and 4,227,992 Garwood, et al., disclose the operating conditions for the Mobil Olefin to Gasoline/Distillate (MOGD) process for selective conversion of $C_3+$ olefins to mainly aliphatic hydrocarbons.

In the process for catalytic conversion of olefins to heavier hydrocarbons by catalytic oligomerization using a medium pore, shape selective, acid, crystalline zeolite, such as ZSM-5 type catalyst, process conditions can be varied to favor the formation of hydrocarbons of varying molecular weight. At moderate temperature and relatively high pressure, the conversion conditions favor $C_{10}+$ aliphatic product. Lower olefinic feedstocks containing $C_2-C_8$ alkenes may be converted; however, the distillate mode conditions do not convert a major fraction of ethylene A typical reactive feedstock consists essentially of $C_3-C_6$ mono-olefins, with varying amounts of nonreactive paraffins and the like being acceptable components.

U.S. Pat. Nos. 4,520,221, 4,568,786 and 4,658,079 to C. S. H. Chen, et al., incorporated herein by reference in their entirety, disclose further advances in zeolite catalyzed olefin oligomerization. These patents disclose processes for the preparation of lubricant range hydrocarbons by oligomerization of light olefins using zeolite catalyst such as ZSM-5. The oligomers so produced are essentially linear in structure and contain 90% internal olefin unsaturation. These unique olefinic oligomers are produced by surface deactivation of the ZSM-5 type catalyst by pretreatment with a surface-neutralizing base. Process conditions can be controlled to favor the recovery of near linear olefin oligomers containing six to twenty carbon atoms. Optionally, lubricant quality oligomers of higher carbon number can also be produced.

It is known that synthetic lubricating fluids of superior quality can be produced by oligomerization of 1-alkenes, particularly 1-decene. Building on that prior art resource, oligomers of 1-alkenes from $C_6$ to $C_{20}$ have been prepared, with commercially useful synthetic lubricants from 1-decene oligomerization yielding a distinctly superior lubricant product via either cationic, Ziegler or chromium catalyst known to be effective in the polymerization of 1-alkenes.

Theoretically, the oligomerization of 1-decene, for example, to lubricant oligomers in the $C_{30}$ and $C_{40}$ range can result in a very large number of structural isomers. Characterizing those oligomers that produce a preferred and superior synthetic lubricant meeting the specification requirements of wide-temperature fluidity while maintaining low pour point represents a prodigious challenge to the workers in the field. Brennan, Ind. Eng. Chem. Prod. Res. Dev. 1980, 19, 2-6, cites 1-decene trimer as an example of a structure compatible with structures associated with superior low temperature fluidity wherein the concentration of atoms is very close to the center of a chain of carbon atoms.

One characteristic of the molecular structure of 1-alkene oligomers that has been found to correlate very well with improved lubricant properties in commercial synthetic lubricants is the ratio of methyl to methylene groups in the oligomer. The ratio is called the branch ratio and is calculated from infra red data as discussed in "Standard Hydrocarbons of High Molecular Weight", Analytical Chemistry, Vol. 25, no. 10, p. 1466 (1953). Viscosity index has been found to increase with lower branch ratio. Oligomers prepared from 1-decene by cationic polymerization have branch ratios of greater than 0.20. Those prepared by chromium or Ziegler catalyzed oligomerization have lower branch ratios. Whether by rearrangement, isomerization or a yet to be elucidated mechanism, it is clear that in the art of 1-alkene oligomerization to produce synthetic lubricants as practiced to-date branching occurs and constrains the limits of achievable lubricant properties, particularly with respect to viscosity index Obviously, increased branching increases the number of isomers in the oligomer mixture, orienting the composition away from the structure which would be preferred from a consideration of the theoretical concepts accepted in the art.

In view of the foregoing, the practice in the synthetic lubricants field has been to oligomerize linear 1-alkene, more particularly single compounds such as 1-decene, in order to help control branching and the number of oligomeric species in the lubricant fluid. However, 1-decene and similar 1-alkenes are expensive and produce expensive lubricant fluids. Unfortunately, potentially less expensive olefins from the process of Chen, et al., are largely internal olefins and are also sightly branched, where unbranched alpha olefins are preferred. Their internal olefin structure also does not lend itself to oligomerization with either Ziegler-Natta or chromium catalysts used to produce very high quality synthetic lubricants. Cationic catalysts, e.g., $BF_3$ or $AlCl_3$ complexes, polymerize internal olefins but result in more branched or lower VI lubes.

Accordingly, it is an object of the present invention to provide a process for the conversion of slightly branched internal olefin oligomers, prepared from lower alkenes using surface deactivated zeolite catalyst, to alpha olefins or 1-alkenes.

Another object of the present invention is to provide a process for converting the aforementioned internal olefins to alpha olefins while retaining the low degree of branching in the internal olefin.

Yet another object of the instant invention is to prepare novel slightly branched 1-alkanol compositions from said internal olefins.

A further object of the present invention is to provide a process for production of less expensive 1-alkenes useful in the preparation of high quality polyalphaolefin (PAO) synthetic lubricant fluids.

SUMMARY OF THE INVENTION

An integrated series of process steps has been discovered that effectively converts internally unsaturated near linear oligomers of lower olefins into alpha olefins, or 1-alkenes, of essentially the same degree of linearity. The internally unsaturated olefins are the product of lower alkene oligomerization using a surface deactivated zeolite, such as ZSM-5 or ZSM-23, and contain about 1 to 2 methyl branches per fifteen carbon atoms. This feedstock is converted in the present invention to alpha olefin oligomers which also contain approximately 1 to 2 methyl branches per fifteen carbon atoms. The conversion is achieved by hydroformylation of the near linear internal olefins to provide a novel 1-alkanol oligomer structure without further branching of the carbon oligomeric chain. Acetylation of the 1-alkanol followed by deesterification by pyrolysis provides the sought for 1-alkene, without increasing the non-linearity of the 1-alkanol. The acetylation can be achieved in situ during the pyrolysis by cofeeding acetic anhydride and the 1-alkanol. In this manner, near-linear oligomers of lower olefins are converted to vinyl hydrocarbon monomers that can be further oligomerized by cationic and coordination catalysts.

More particularly, a process is disclosed for the production of near linear 1-alkene comprising vinyl hydrocarbon monomer, or a mixture of vinyl monomers, from near linear lower alkene oligomer having between six and twenty carbon atoms and containing internal olefinic unsaturation. The process comprises reacting the oligomer, or a mixture of oligomers, with $H_2$ and CO mixture in contact with a hydroformylation catalyst under hydroformylation conditions sufficient to convert the oligomer to aliphatic 1-alkanol. The 1-alkanol contains a methyl to methylene branch ratio equal to or less than the oligomer. The 1-alkanol is recovered by conventional means and converted to an ester under esterification conditions in contact with an aliphatic acylating agent. The ester is recovered and deesterified by pyrolyzing the ester under conditions sufficient to produce 1-alkene comprising near linear vinyl hydrocarbon monomer, or a mixture of monomers.

Preferably, the oligomer comprises the oligomerization product of $C_3$–$C_5$ alkene in contact with surface deactivated, acidic, shape selective, medium pore metallosilicate and has a methyl to methylene branch ratio less than 0.21. The hydroformylation is carried out using a sterically hindered catalyst such as $Co_2(CO)_6[(n\text{—}C_4H_9)_3P]_2$.

The invention also provides a novel mixture of near linear aliphatic 1-alkanols containing between six and twenty carbon atoms and having a methyl to methylene branch ratio less than 0.21. Preferably, the alkanols comprise $C_9$–$C_{12}$ 1-alkanols having a methyl to methylene branch ratio less than 0.18.

DETAIL DESCRIPTION OF THE INVENTION

Near linear alpha olefins are produced in the present invention according to the following general sequence of reactions where R is the olefin oligomer hydrocarbyl moiety:

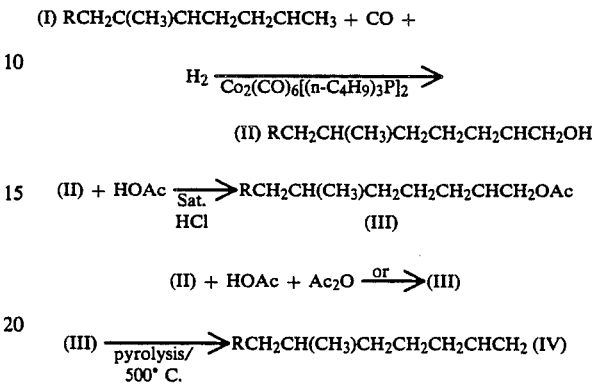

(I) $RCH_2C(CH_3)CHCH_2CH_2CHCH_3$ + CO +

$$H_2 \xrightarrow{Co_2(CO)_6[(n\text{-}C_4H_9)_3P]_2}$$

(II) $RCH_2CH(CH_3)CH_2CH_2CH_2CHCH_2OH$ (II) + HOAc $\xrightarrow[\text{HCl}]{\text{Sat.}}$ $RCH_2CH(CH_3)CH_2CH_2CH_2CHCH_2OAc$ (III)

(II) + HOAc + $Ac_2O$ $\xrightarrow{\text{or}}$ (III)

(III) $\xrightarrow[500^\circ C.]{\text{pyrolysis/}}$ $RCH_2CH(CH_3)CH_2CH_2CH_2CHCH_2$ (IV)

NEAR-LINEAR OLEFIN

The olefin oligomers used as starting material in the present invention are prepared from $C_3$–$C_5$ olefins according to the methods presented by Chen, et al., in the aforementioned patents cited and N. Page and L. Young in allowed application Ser. No. 105,438, filed Oct. 7, 1987 and incorporated herein as references. Shape-selective oligomerization, as it applies to conversion of $C_3$–$C_5$ olefins over ZSM-5, is known to produce higher olefins up to $C_{30}$ and higher. Reaction conditions favoring higher molecular weight products are low temperature (200°–260° C.), elevated pressure (about 2000 kPa or greater) and long contact times (less than 1 WHSV). The reaction under these conditions proceeds through the acid catalyzed steps of oligomerization, isomerization-cracking to a mixture of intermediate carbon number olefins, and interpolymerization to give a continuous boiling product containing all carbon numbers. The channel system of ZSM-5 type catalysts impose shape selective constraints on the configuration of large molecules, accounting for the differences with other catalysts The shape-selective oligomerization/polymerization catalysts preferred for use herein to prepare the olefin oligomers used as starting material in the invention include the crystalline aluminosilicate zeolites having a silica to alumina molar ratio of at least 12, a constraint index of about 1 to 12 and acid cracking activity of about 50–300. Representative of the ZSM-5 type zeolites are ZSM-5, ZSM-11, ZSM-12, ZSM-23, ZSM-35 and ZSM-38. ZSM-5 is disclosed and claimed in U.S. Pat No. 3,702,886 and U.S. Pat. No. Re. 29,948; ZSM-11 is disclosed and claimed in U.S. Pat. No. 3,709,979. Also, see U.S. Pat. Nos. 3,832,449 for ZSM-12; 4,076,842 for ZSM-23; 4,016,245 for ZSM-35 and 4,046,839 for ZSM-38. The disclosures of these patents are incorporated herein by reference. A suitable shape selective medium pore catalyst for fixed bed is a small crystal H-ZSM-5 zeolite (silica:alumina ratio=70:1) with alumina binder in the form of cylindrical extrudates of about 1–5 mm. Unless otherwise stated in this description, the catalyst shall consist essentially of ZSM-5, which has a crystallite size of about 0.02 to 0.05 micron, or ZSM-23. Other pentasil catalysts which may be used in one or more reactor stages include a variety of medium pore siliceous material disclosed in U.S. Pat. Nos. 4,414,423 and 4,417,088, incorporated herein by reference.

The acid catalysts are deactivated by pretreatment with a surface-neutralizing base, as disclosed by Chen, et al., and Page, et al., in the patent and allowed application incorporated by reference. Surface deactivation is carried out using bulky or sterically hindered bases, typically those comprising trialkyl substituted pyridines. These hindered bases have very limited access to the internal pore structure of the catalyst, leaving the pores active sites for near linear oligomerization. However, active surface sites which are not constrained, as pores are, to low branching oligomerization are neutralized.

Considering propylene oligomerization for purposes of illustration, the olefinic oligomerization-polymerization products include $C_{10}+$ substantially linear aliphatic hydrocarbons. The ZSM-5 catalytic path for propylene feed provides a long chain with approximately one lower alkyl (e.g., methyl) substituent per 8 or more carbon atoms in the straight chain.

When propylene or butene are oligomerized according to processes described herein, a unique mixture of liquid hydrocarbon products are formed. More particularly, this mixture of hydrocarbons may comprise at least 95% by weight of mono-olefin oligomers of the empirical formula:

$$C_nH_{2n}$$

where n is 3 to 30, the mono-olefin oligomers comprising at least 20 percent by weight of olefins having at least 12 carbon atoms, the olefins having at least 12 carbon atoms having an average of from 0.80 to 2.00 methyl side groups per carbon chain, the olefins not having any side groups other than methyl.

It will be understood that methYl side groups are methyl groups which occupy positions other than the terminal positions of the first and last (i.e., alpha and omega) carbon atoms of the longest carbon chain. This longest carbon chain is also referred to herein as the carbon backbone chain of the olefin. The average number of methyl side groups for the $C_{12}$ olefins may comprise any range with the range of 0.80 to 2.00.

These oligomers may be separated into fractions by conventional distillation separation When propylene is oligomerized, olefin fractions containing the following number of carbon atoms can be obtained 6, 9, 12, 15, 18 and 21. When butene is oligomerized, olefin fractions containing the following numbers of carbon atoms may be obtained 8, 12, 16, 20, 24 and 28. It is also possible to oligomerize a mixture of propylene and butene and to obtain a mixture of oligomers having at least 6 carbon atoms.

Page and Young (allowed application Ser. No. 105,438, filed Oct. 7, 1987) described these new olefins as multi-component mixtures of propylene oligomers having relatively few branching methyl groups on the carbon backbone. As an example of branching, the dodecene fraction prepared from propylene and HZSM-23 surface modified by collidine [ZSM-23-dodecenes] typically has 1.3 methyl branches. This can be reduced to 1.0 or less by varying reaction conditions.

HYDROFORMYLATION

Hydroformylation, a rhodium or cobalt catalyzed addition of carbon monoxide and hydrogen gas to an olefin, produces aldehydes. See J. Falbe, *New Syntheses with Carbon Monoxide*, New York (1980); E. J. Wickson, *Monohydric Alcohols*, ACS Symposium Series 159, Washington, D.C. (1981); Ford, P. C., *Catalytic Activation cf Carbon Monoxide*, ACS Symposium Series 152, Washington, D. C. (1981), all references hereby incorporated by reference. However, Slaugh and Mullineaux discovered that hydroformylations using complexes of tri-n-butylphosphine and cobalt carbonyl catalyze the conversion of olefins directly to alcohols (i.e., the initially formed aldehydes concurrently hydrogenate). Also, the new alcohol function (—CH$_2$OH) bonds predominately on the carbon chain-end. See Slaugh, L., Mullineaux, R. D., *Hydroformylation Catalysts*, J. Organomet. Chem., 13, 469–477 (1968); U.S. Pat. Nos. 3,239,569; 3,239,570; 3,329,566; 3,488,158; and 3,488,157, all references hereby incorporated by reference. This permits using a variety of internal olefins as feeds, because they isomerize to a terminal position before hydroformylating. In contrast, rhodium-based catalysts do not promote olefin isomerization, and hydroformylation occurs predominately on the original double bond. See Asinger, F., Fell, B., Rupilius, W., *Hydroformylation of 1-Olefins in Tertiary Orqanophosphine-Colbalt Hydrocarbonyl Catalyst Systems*, Chem. Process Des. Dev., 8(2), 214 (1969); Stefani, A., Consiglio, G., Botteghi, C., Pino, P., *Stereochemistry of the Hydroformylation of Olefinic Hydrocarbons with Cobalt and Rhodium Catalysts*, J. Amer. Chem. Soc., 99(4), 1058–1063.

ESTERIFICATION

The formation of esters from primary alcohols analogous to the hydroformylation product of the near-linear olefins described above is a reaction well known in the art. The 1-alkanols used in the present invention can be converted to esters using acylating agents that include aliphatic carboxyl acids, acyl halides, carboxyl acid anhydrides or corboxyl acid esters. Other, less common, routes to esterification may also be used such as those using ketenes and alcoholysis of nitriles. The art is well described in "Synthetic Organic Chemistry" by Wagner and Zuck, published by John Wiley and Sons, pages 480–498, incorporated herein by reference.

Acylating agents used in the present invention comprise aliphatic carboxyl acids and derivatives thereof having $C_1$-$C_{20}$ carbon atoms, particularly carboxyl acid anhydrides. The preferred acylating agent is acetic anhydride which converts the primary alcohol of the invention to the acetate ester. The reaction is typically carried out in the presence of a catalyst such as small amounts of sulfuric acid, sodium acetate, pyridine or Al$_2$O$_3$. Generally, the esters are formed using carboxyl acid derivatives containing 2 to 6 carbon atoms and, in addition to acetic acid, include proprionic and buturic acid.

PYROLYSIS

The final synthetic step in the synthesis of the alpha-olefins according to the present invention involves the conversion of the aforementioned esters to the alpha-olefin by pyrolysis or deesterification. It is known in the art that olefins, including alpha-olefins can be produced by dehydration of primary alcohols typical of those produced in this invention. However, an important consideration in the present invention is to conduct all the processes including this final synthetic step without increasing the branching of the oligomeric molecule. Maintaining linearity in order to produce near-linear alpha-olefins is an important part of the overall inventive concept. Directly dehydrating the alkanol can, in some cases, lead to isomerization which may increase branching. This possibility is obviated by preparing the alpha-olefin by deesterification which does not result in isomerization or increased branching of the alpha-olefin.

The pyrolysis of esters to olefins is known in the art and described in "Synthetic Organic Chemistry" by Wagner and Zuck, John Wiley and Son, Publisher, pages 41-42, incorporated herein by reference. Pyrolysis can be carried out at temperatures between 300°-750° C. to yield the olefin, in this case alpha-olefin, in high yield.

As previously described herein the near-linear olefins used as starting material in this invention are typically prepared comprising a mixture of olefins containing a wide range of carbon numbers. The starting material may be used in this condition to produce a mixture of 1-alkanols and alpha-olefins containing a wide range of carbon numbers. Optionally the near-linear olefins can be separated by distillation or other means common and known in the art to narrow the range of carbon numbers in the starting material. For purposes of utilizing the present invention to prepare alpha-olefins suitable for oligomerization to synthetic lubricants carbon numbers in the range of $C_9$-$C_{12}$ are preferred. A more particularly preferred carbon number for an alpha-olefin is 1-decene.

The following prophetic Examples are presented to illustrate the overall process of the present invention and are not intended to limit the scope of the invention.

EXAMPLE 1

(a) Near-linear olefins are prepared from propylene or isobutene or refinery mixtures of propylene, butenes, propane and butanes using 2,6-di-tert-butylpyridine surface deactivated HZSM-5B as the shape selective catalyst according to the procedure described in U.S. Pat. No. 4,520,221.

(b) The above olefins are hydroformylated at 180° C. using a mixture of carbon monoxide and hydrogen and $Co_2(CO)_6[(n-C_4H_9)_3P]_2$ as catalyst. The hydroformylation is carried out under these conditions for a period of time sufficient to convert the near-linear olefins starting material to a mixture of 1-alkanols.

(c) The 1-alkanols from (b) are separated by distillation and esterified using acetic acid and $A_2O_3$ as catalyst to produce the acetate ester of the 1-alkanols.

(d) The acetate esters prepared in (c) are separated and pyrolyzed at 500° C. over pyrexhelices to produce a mixture of alpha-olefins having a methyl to methylene branch ratio of 0.15 to 0.25.

EXAMPLE 2

(a) Near-linear olefins with 1 to 2 methyl branches per 12 carbon atoms are prepared by propylene or refinery mixtures of propylene, butenes, propane and butane using 2,4,6-collidine modified HZSM-23 as the shape selective catalyst according to procedures described by Page and Young in the reference previously cited herein. Hydroformylation, esterification and pyrolysis steps are carried out as described in steps (b), (c) and (d) in Example 1. The alpha olefins produced have a methyl to methylene branch ratio of 0.1 to 0.2.

EXAMPLE 3

1-alkanols are prepared as described in step (b) of Example 1. In a continuous process the 1-alknaols are reacted with an excess of acetic anhydride and passed over silica at 600° C., in a nitrogen atmosphere, to pyrolyze the acetate ester formed in situ to alpha-olefins having a methyl to methylene branch ratio of 0.15 to 0.25.

EXAMPLE 4

1-alkanols are prepared as described in step (b) of Example 2. In a continuous process the 1-alkanols are reacted with an excess of acetic anhydride and passed over silica at 600° C., in a nitrogen atmosphere, to pyrolyze the acetate formed in situ to alpha olefins having a methyl to methylene branch ration of 0.1 to 0.2.

The branch ratios defined as the ratios of $CH_3$ groups to $CH_2$ groups are calculated from the weight fractions of methyl groups obtained by infrared methods, published in *Analytical Chemistry.* Vol. 25, No. 10, p. 1466 (1953).

$$\text{Branch ratio} = \frac{\text{wt fraction of methyl group}}{1 - (\text{wt fraction of methyl group})}$$

While the instant invention has been described by specific examples and embodiments, there is no intent to limit the inventive concept except as set forth in the following claims.

What is claimed is:

1. A process for the production of near linear 1-alkene from near linear lower alkene oligomer having between six and twenty carbon atoms, said oligomer containing internal olefinic unsaturation, comprising;
   reacting said oligomer with $H_2$ and CO mixture in contact with a hydroformylation catalyst under hydroformylation conditions sufficient to convert said oligomer to aliphatic 1-alkanol, said alkanol having a methyl to methylene branch ratio equal to or less than said oligomer;
   recovering and converting said 1-alkanol to an ester under esterification conditions in contact with aliphatic acylating agent;
   recovering and pyrolyzing said ester under conditions sufficient to produce said 1-alkene.

2. The process of claim 1 wherein said oligomer comprises the oligomerization product of $C_3$-$C_5$ alkene in contact with surface deactivated, acidic, shape selective, medium pore metallosilicate.

3. The process of claim 2 wherein said oligomer comprises the oligomerization product of propylene.

4. The process of claim 1 wherein said oligomer and said 1-alkene methyl to methylene branch ratio is less than 0.25.

5. The process of claim 4 wherein said ratio is between 0.1 and 0.2.

6. The process of claim 1 wherein the branch ratio of said 1-alkene is not greater than that of said oligomer.

7. The process of claim 1 wherein said oligomer comprises $C_9$-$C_{12}$ hydrocarbon having methyl to methylene branch ratio of less than 0.18.

8. The process of claim 1 wherein said hydroformylation catalyst comprises one of rhodium, cobalt and ruthenium.

9. The process of claim 7 wherein said catalyst comprises $Co_2(CO)_6[(n-C_4H_9)_3P]_2$.

10. The process of claim 1 wherein the $H_2/CO$ ratio is in the range of 0.5:1 to 5:1.

11. The process of claim 10 wherein said ratio is about 1.8 to 1.

12. The process of claim 1 wherein said hydroformylation conditions comprise temperature between 250° and 150° C.

13. The process of claim 12 wherein the temperature is about 181° C.

14. The process of claim 1 wherein said acylating agent comprises aliphatic carboxylic acid, anhydride, halide or ester having 2 to 20 carbon atoms.

15. The process of claim 1 wherein said acylating agent comprises acetic anhydride and said ester comprises acetate.

16. The process of claim 1 wherein said ester is pyrolyzed at a temperature between 200° and 800° C.

17. The process of claim 16 wherein the temperature is about 500° C.

18. A mixture of near linear 1-alkenes having between seven and twenty-one carbon atoms, said alkenes comprising the reaction product of the process comprising;
    reacting a feedstock comprising near linear lower alkene oligomers having between six and twenty carbon atoms, said oligomers containing internal olefinic unsaturation, with $H_2$ and CO mixture in contact with a hydroformylation catalyst under hydroformylation conditions sufficient to convert said oligomers to near linear aliphatic 1-alkanols, said alkanols having a methyl to methylene branch ratio equal to or less than said oligomers;
    recovering and converting said 1-alkanols to esters under esterification conditions in contact with aliphatic acylating agent;
    recovering and pyrolyzing said esters under conditions sufficient to produce said 1-alkenes.

19. The mixture of claim 18 wherein said oligomers contain between nine and twelve carbon atoms and said 1-alkenes comprise $C_{10}$–$C_{13}$ 1-alkenes having a methyl to methylene branch ratio of less than 0.18.

20. The mixture of claim 18 wherein said hydroformylation catalyst comprises one of rhodium, cobalt and ruthenium.

21. The mixture of claim 20 wherein said catalyst comprises $Co_2(CO)_6[(n-C_4H_9)_3P]_2$.

22. The mixture of claim 20 wherein the $H_2/CO$ ratio is in the range of 0.5:1 to 5:1.

23. The mixture of claim 22 wherein said ratio is about 1.8 to 1.

24. The mixture of claim 18 wherein said hydroformylation conditions comprise temperature between 250° and 150° C.

25. The mixture of claim 24 wherein the temperature is about 181° C.

26. The mixture of claim 18 wherein said acylating agent comprises aliphatic carboxylic acid, anhydride, halide or ester having 2 to 20 carbon atoms.

27. The mixture of claim 18 wherein said acylating agent comprises acetic anhydride and said ester comprises acetate.

28. The mixture of claim 18 wherein said ester is pyrolyzed at a temperature between 200° and 800° C.

29. The process of claim 28 wherein the temperature is about 500° C.

* * * * *